(12) United States Patent
Woodward et al.

(10) Patent No.: US 7,793,907 B2
(45) Date of Patent: Sep. 14, 2010

(54) MONITOR SUSPENSION DEVICE AND METHOD OF USE

(76) Inventors: Robert Woodward, 1149 E. 900 South, Salem, UT (US) 84653; Creed Larsen, 159 S. Pleasant Grove Blvd., #19, Pleasant Grove, UT (US) 84062

( * ) Notice: Subject to any disclaimer, the term of this patent is extended or adjusted under 35 U.S.C. 154(b) by 330 days.

(21) Appl. No.: 11/788,471

(22) Filed: Apr. 20, 2007

(65) Prior Publication Data

US 2008/0259541 A1 Oct. 23, 2008

(51) Int. Cl.
*A47H 1/00* (2006.01)
(52) U.S. Cl. .................... 248/317; 248/917; 248/919
(58) Field of Classification Search ............ 248/317, 248/232, 917–923; 361/681; 414/140.2
See application file for complete search history.

(56) References Cited

U.S. PATENT DOCUMENTS

| | | | | |
|---|---|---|---|---|
| 4,868,845 | A * | 9/1989 | Koropp | 378/204 |
| 5,405,117 | A * | 4/1995 | Davis | 248/333 |
| 6,158,704 | A * | 12/2000 | O'Neill | 248/317 |
| 6,318,692 | B1 * | 11/2001 | Cyrell | 248/317 |
| 7,134,719 | B2 * | 11/2006 | Moglin et al. | 297/217.3 |
| 7,377,475 | B1 * | 5/2008 | Lopez | 248/323 |
| 7,455,535 | B2 * | 11/2008 | Insalaco et al. | 439/121 |

* cited by examiner

*Primary Examiner*—Amy J Sterling
(74) *Attorney, Agent, or Firm*—Jones Waldo Holbrook & McDonough

(57) ABSTRACT

A monitor suspension system, the system in its various embodiments including a suspension arm having a first and second end; a component housing coupled to the first end of the suspension arm, and wherein the component housing is capable of being further coupled to one or more monitors. A lateral carriage assembly is also coupled to the second end of suspension arm. The lateral carriage assembly can include a first lateral track; a lateral trough coupled to the first lateral track; a second lateral track; and a lateral movement piece which is slidably coupled between the first lateral track and the second lateral track. A first and optional second backward/forward track are slidably engaged by the lateral carriage by means of a first and second front/back sliding assembly coupled to the lateral carriage assembly. A backward/forward trough is coupled to one of the backward/forward tracks. A first cable chain is coupled at a first end to the backward/forward trough and coupled at a second end to the lateral carriage assembly. A second cable chain is coupled at a first end to the lateral trough and coupled at a second end to the lateral movement piece.

17 Claims, 19 Drawing Sheets

MONITOR SUSPENSION DEVICE AND METHOD OF USE

BACKGROUND

In the world of healthcare, monitors are often used in a variety of settings. For example, LCD monitors are used to display a patient's vital signs such that they are clearly visible to the attending physician or other healthcare professional. Other monitors are used to display video images as are needed from time to time in a variety of procedures.

Whatever the specific purpose, monitors are an essential piece of medical equipment these days. That notwithstanding, the current state of the art in medical monitor technology is not very practical at all. Specifically, present-day medical monitors are typically LCD monitors having arm attachments whereby they can be mounted on the ceiling or a wall of the room in which they are being utilized. As can be appreciated, these monitors are coupled to the various pieces of equipment and/or power supply through a series of cables and cords. These cables and cords are sometimes bundled into vacuum tubing and directed to the various components they service.

Often, these cables and cords must extend for several feet. As can be appreciated, having numerous electric cords strewn about a medical procedure room is not only unsightly, but can be potentially dangerous. Moreover, the present state of the art does not adequately allow for servicing of the cables when they are bundled in vacuum tubes. For example, if one of the cables was to malfunction, remedying the problem would be exceedingly difficult. Under the present state of the art, one could attempt to simply remove the malfunctioning cable, but that would leave the difficult task of extracting it from the bundle of cords in the vacuum tube—where tangles would be a frequent occurrence. Additionally, once the cord was removed, to thread a new cord back through would be nigh impossible.

Beyond that, a cable malfunction is often a localized problem requiring only a localized solution (rather than complete replacement of the cable). Again, having the cords bundled into a vacuum tube is not conducive to localized repair of the cables.

Another problem with the present state of the art is that the monitors are not easily relocated. Specifically, the mounting arms are for the most part stationary. Those that do provide some range of motion are for only very limited up/down and pivotal side to side motion. Clearly, such a narrow range of motion is not desirable as the medical situations requiring monitors can widely differ—thus requiring a different set up of the examination room; operating room, etc.

Another limitation with the present state of the art is that current monitor suspension systems are very heavy. As can be appreciated, a heavy piece of equipment hanging from the ceiling (or wall as the case may be) can also present a significant danger if not properly installed.

All of the foregoing shortcomings, as well as many others, are addressed by the present invention in its various embodiments.

SUMMARY OF THE INVENTION

The invention as presently claimed is for a monitor suspension system. The system includes a suspension arm having a first and second end. A component housing is coupled to the first end of the suspension arm. The component housing is capable of being further coupled to one or more monitors. A lateral carriage assembly is coupled to the second end of suspension arm. The lateral carriage assembly includes a lateral track; a lateral trough coupled to the lateral track; and a lateral movement piece which is slidably coupled to the lateral track. The system also includes a backward/forward track and a backward/forward trough coupled to the backward/forward track. A front/back sliding assembly is coupled to the lateral carriage assembly and capable of slidably engaging the front/back track. The system can include a second lateral track running substantially parallel to the lateral track. In one embodiment, the lateral movement piece is slidably coupled between the lateral track and the second lateral track.

The system can also include a second backward/forward track. In one embodiment, the lateral carriage assembly is slidably coupled to the backward/forward track and the second backward/forward track. The lateral carriage assembly can be slidably coupled to the backward/forward track and the second backward/forward track by front/back sliding assemblies. These assemblies can be coupled to the lateral carriage assembly and are capable of slidably engaging the front/back track and the second front/back track. In one embodiment, a first cable chain is coupled at a first end to the backward/forward trough and coupled at a second end to the lateral carriage assembly. A second cable chain can also be coupled at a first end to the lateral trough and coupled at a second end to the lateral movement piece.

The component housing can include an actuator allowing for up and down movement of the one or more monitors. In one embodiment, the actuator includes an actuator screw; a motor; and a screw engagement piece. The component housing can also include one or more secondary cable chains.

DETAILED DESCRIPTION OF THE DRAWINGS

Figure 1:
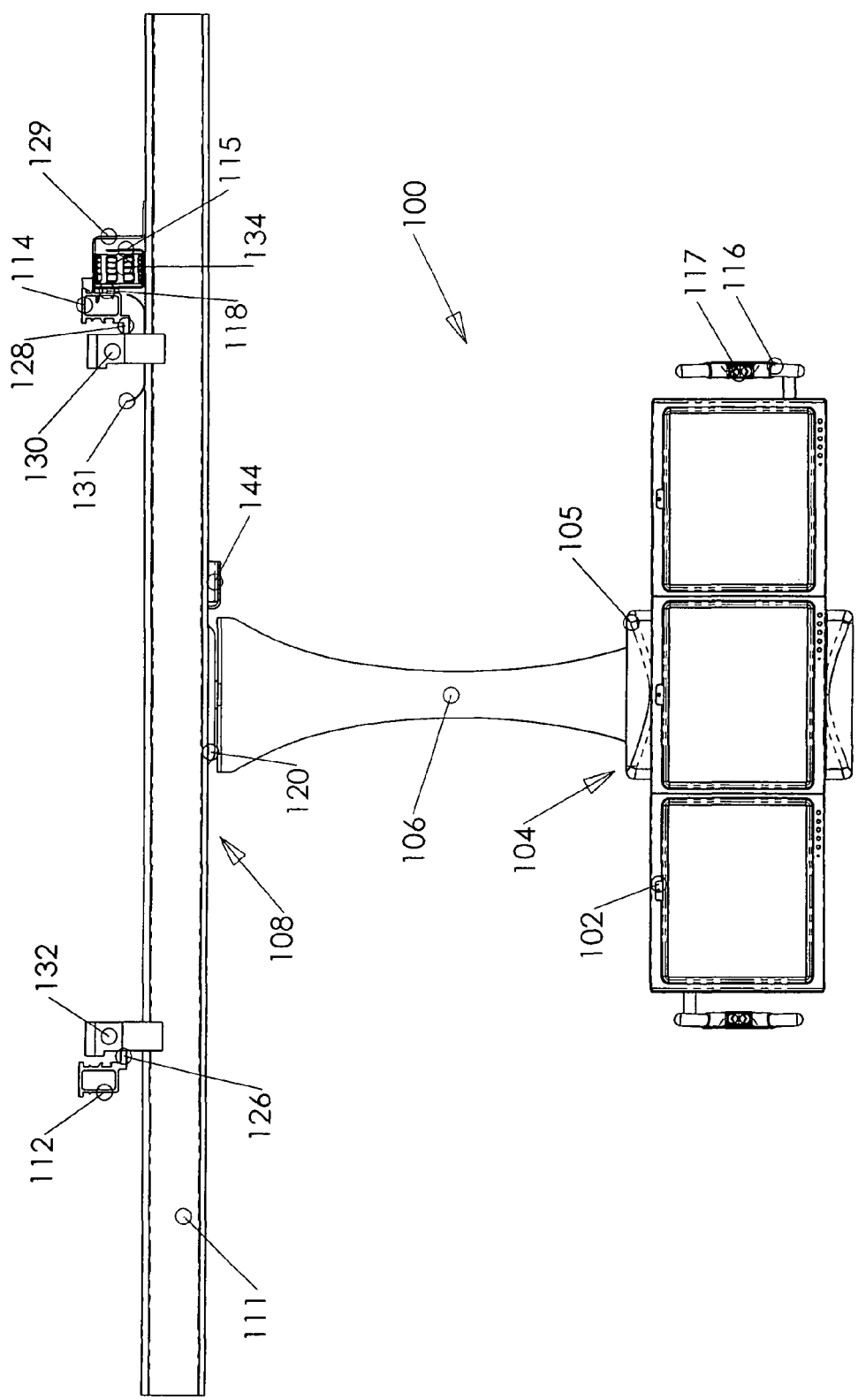
FIG. 1 shows a front view of a medical monitor suspension system according to one embodiment of the present invention.

Referring to FIGS. 1-4, there is shown a medical monitor suspension system 100 according to one embodiment of the present invention. The suspension system 100 includes a suspension arm 106 coupled at one end to a component housing 104. The component housing 104 is then further coupled to one or more monitors 102. The housing 104 can include one or more handles 116 to assist in moving the monitors. At its other end, the suspension arm 106 is coupled to a lateral carriage assembly 108.

Figure 2:
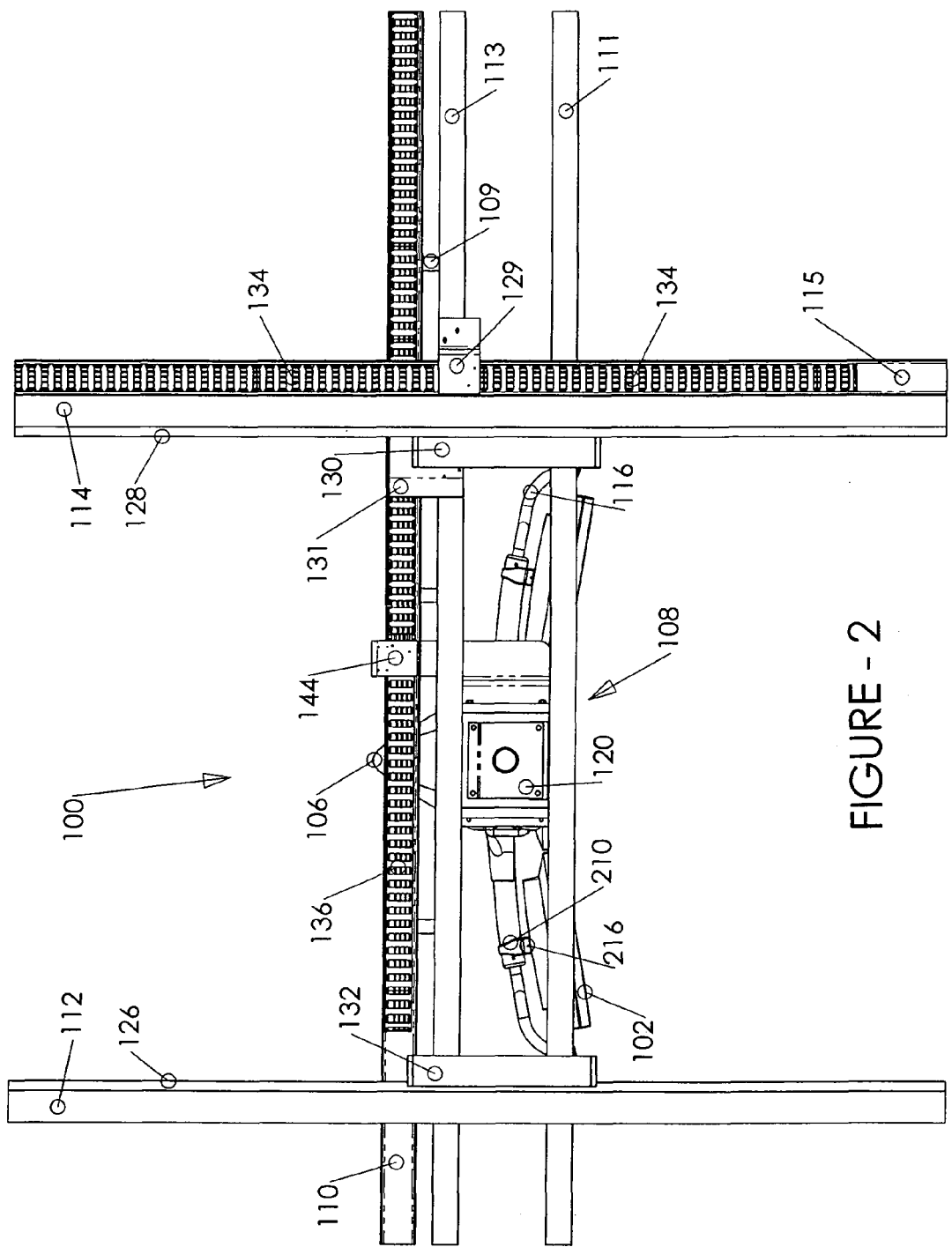
FIG. 2 shows a top view of the system depicted in FIG. 1.
Figure 3:
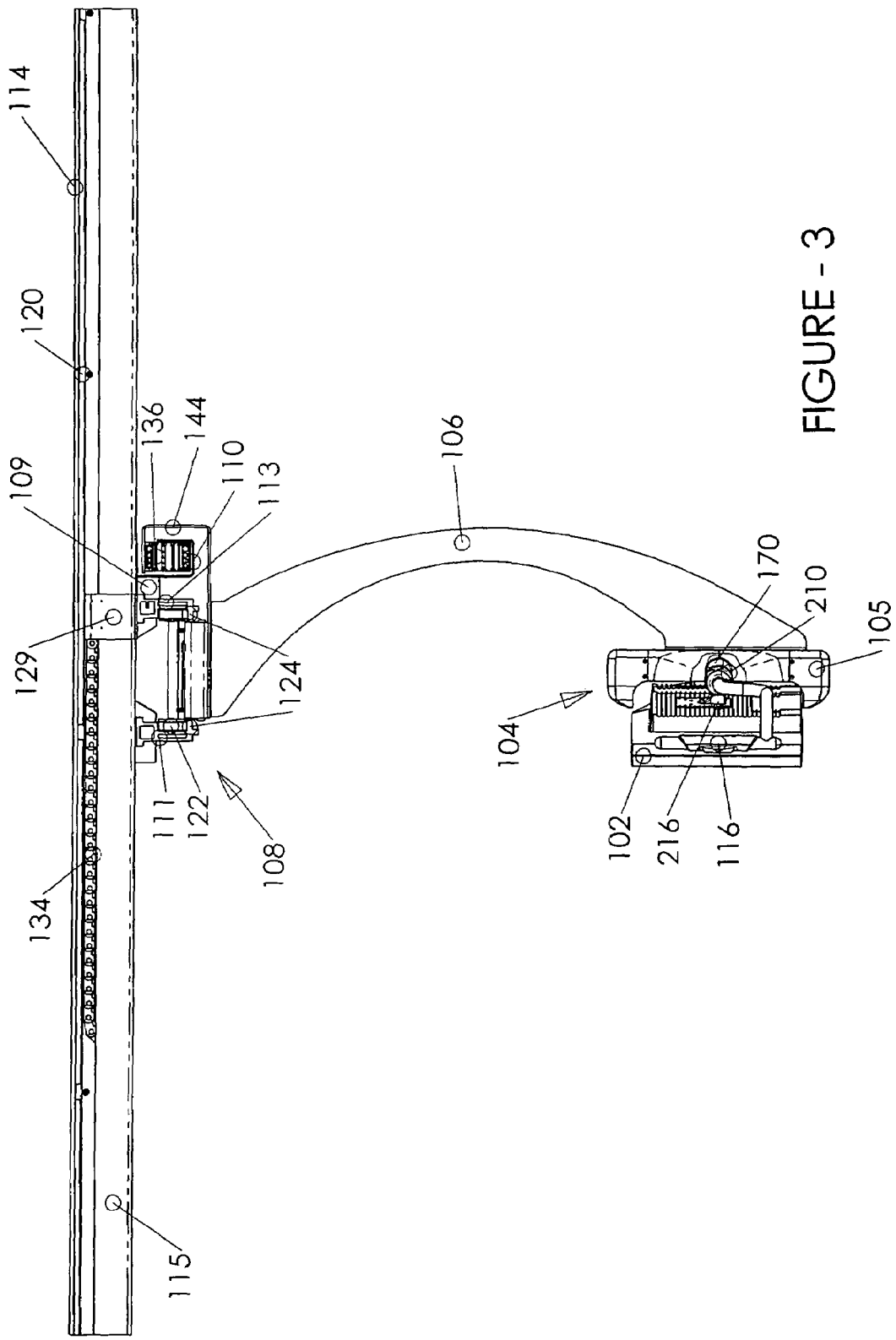
FIG. 3 shows a side view of the system depicted in FIG. 1.

As better seen in FIGS. 2 and 3, the lateral carriage assembly 108 includes a front lateral track 111 and a rear lateral track 113. In this embodiment, a lateral trough 110 is coupled to the rear lateral track 113. However, it is noted that in other embodiments, the trough 110 could be coupled to the front lateral track 111. The carriage assembly 108 also includes a lateral movement piece 120 which is slidably coupled between the front lateral track 111 and the rear lateral track 113. The lateral movement piece 120 in this embodiment includes wheels 122 which slidably move along grooves 124 in front and rear tracks 111, 113.

The trough 110 is coupled to the rear lateral track 113 through coupling 109. In the present embodiment, the coupling is an aluminum mounting block, which further serves to provide some space between the trough 110 and the track 113. However, as would be apparent to one of skill in the art, numerous other mechanisms could be employed for coupling the trough 110 to the track 113. In one embodiment, the trough 110 and track 113 could be manufactured as a single piece. In such a case, the trough 110 would still be considered to be effectively "coupled to the track."

It is noted that the term "trough" is intended to encompass any sort of channeling piece through which the necessary cable chains (as discussed further below) can be directed. It is also noted that the term "track" includes a wide variety of mechanisms whereby the lateral movement piece 120 can be slidably engaged as would be apparent to one skilled in the art. It is also noted that in some embodiments, the trough 110 could be independently mounted to the structure in which it is installed, but run alongside the track 111 (or 113 in certain embodiments). It is noted that in such a case, the trough 110 would still be considered to be effectively "coupled to the track."

The lateral carriage assembly 108 is slidably coupled to tracks 112, 114. These tracks allow for backward and forward movement of the lateral carriage assembly 108. However, it is noted that the terms "backwards" and "forwards" as they relate to tracks 112, 114 are merely to illustrate that tracks 111, 113 direct movement in a substantially perpendicular direction to tracks 112, 114. However, depending on the orientation of the suspension system 100, movement may or may not actually be backwards or forwards.

In this embodiment, the tracks 112, 114 are mounted on the ceiling. However, as can be appreciated to one of ordinary skill in the art, the tracks 112, 114 could be coupled, directly or indirectly, to any overhead structure such as the framing of the building into which it is installed.

As can better be seen in FIGS. 1, 4, 16 and 17, tracks 112, 114 include grooves 126, 128 respectively. Into these grooves 126, 128 sliding assemblies 132, 130 engage allowing backward and forward movement of the lateral carriage assembly 108. In this embodiment, the sliding assemblies 132, 130 include roller bearings that engage the tracks 112, 114. However, it is noted that numerous other slidable engagements would be apparent to one of ordinary skill in the art and would be suitable for use in the present system. For example, the sliding assemblies 132, 130 could be coated in Teflon (the tracks 112, 114 could likewise be Teflon-coated), such that the assemblies 132, 130 simply slide over the tracks 112, 114 by means of the low friction surface.

Coupled to track 114 is trough 115. However, it is noted that in other embodiments, the trough 115 could be coupled to track 112. The track 114 and trough 115 are coupled together with coupling 118. In the present embodiment, this coupling 118 is an aluminum mounting block, however, as would apparent to one skilled in the art, this coupling could be accomplished by numerous other mechanisms. As was noted in the context of the lateral carriage assembly 108, the term "trough" is intended to encompass any sort of channeling piece through which the necessary cable chains (as discussed further below) can be directed. It is also noted that the term "track" includes a wide variety of mechanisms whereby the lateral carriage assembly 108 can be slidably engaged that would be apparent to one skilled in the art.

The monitor suspension system 100 can also include cable chain 134 through which a variety of cables can be directed—including, but not limited to power supply cables, video feed cables, network cables, or other data cables. As is better seen in FIGS. 16 and 17, the cable chain 134 is coupled at a first end to the backward/forward trough 115 at point 140. It is coupled at a second end to support piece 129—which is in turn coupled to the lateral carriage assembly 108. Thus, the support piece 129 links the lateral carriage assembly 108 with the backward/forward trough 115 and the cable chain 134 therein. Support piece 129 also secures the cable chain 134 inside the trough 115 and further facilitates the proper passage of the cable chain 134 through the trough 115.

The cable chain 134 in this embodiment is B15i-050-038-0 available from Igus, Inc. (E. Providence, R.I.). Other types of cable chain suitable for use with the present invention include, but are not limited to Z14-4-028-0, 15-050-038-0, and 02914s (all available from Igus, Inc.).

Another length of cable chain 136 is directed through the lateral trough 110. This second cable chain 136 is coupled at a first end to the lateral trough 110 at point 107 and coupled at a second end to support piece 144—which is in turn coupled to the lateral movement piece 120. It is noted that as used herein, the term "coupled" means both directly coupled and/or indirectly coupled. Regardless of the exact nature of the coupling, what is important is that when the lateral movement piece 120 moves, that movement is translated to the cable chain 136. The same is true for the front/back chain 134—i.e. coupled does not necessarily mean directly coupled. So long as the movement of the lateral carriage assembly 108 is translated along to the chain 134.

Figure 4:
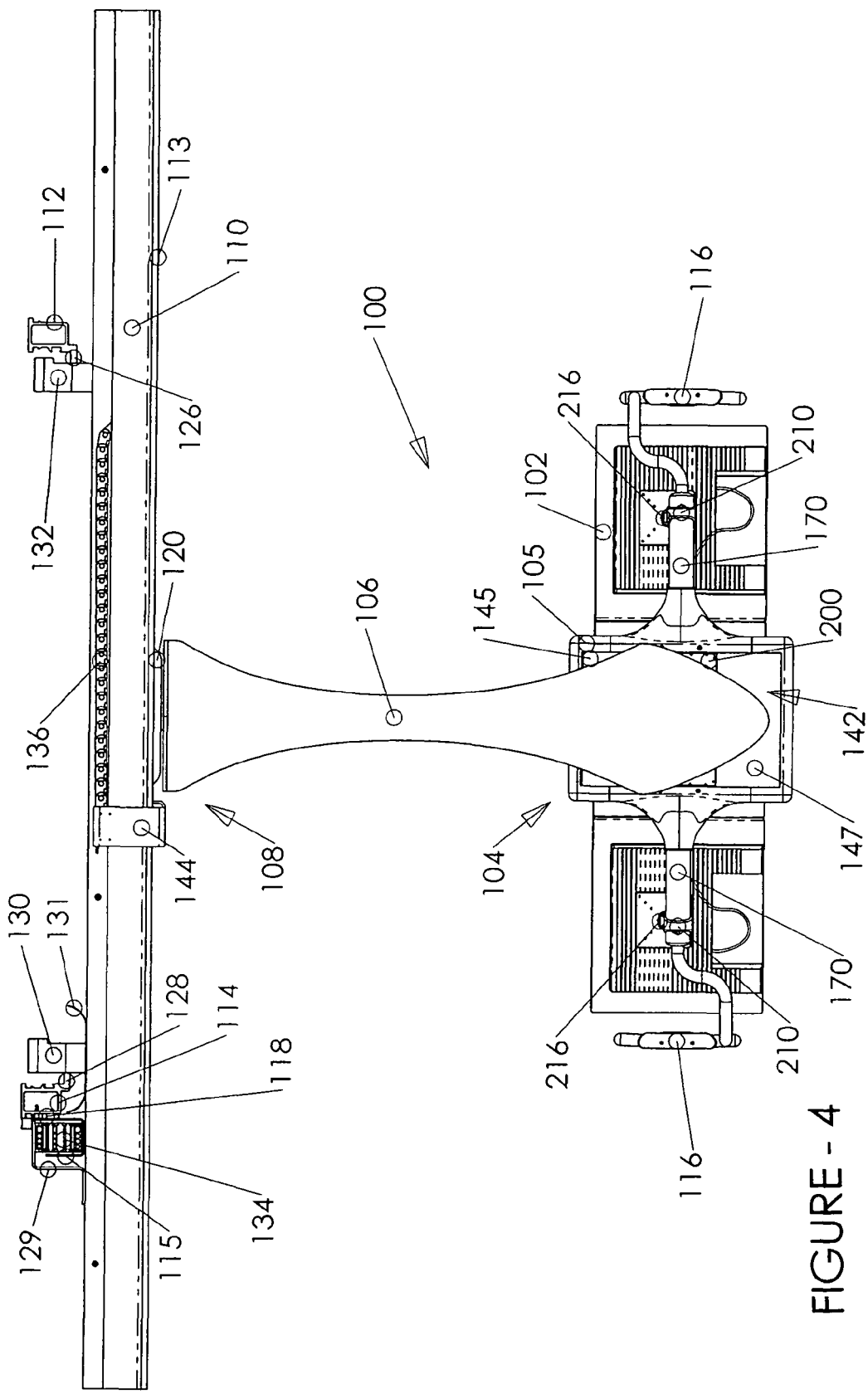
FIG. 4 shows a backside view of the system depicted in FIG. 1.

As is better seen in FIGS. 1, 2 and 4, sliding assembly 130 can also include a guide 131. The guide 131 helps keep the cable chain 136 in place in the trough 110 as the lateral movement piece 120 slid from side to side.

Figure 17:
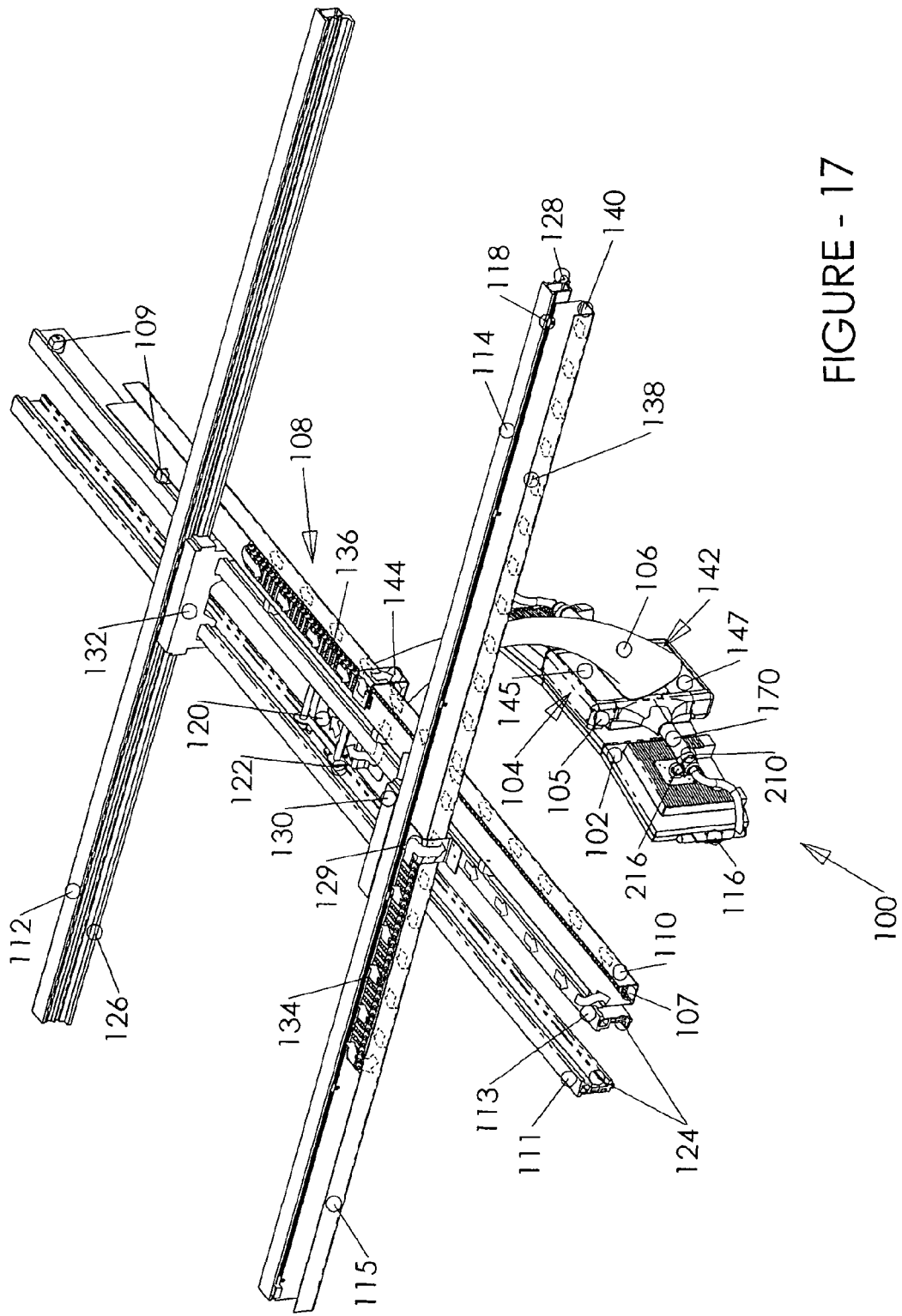
FIG. 17 illustrates the movement of the cable chain according to one embodiment of the present invention.

FIG. 17, illustrates the direction of the cables running through the system. The cables enter at point 140 of the trough 115 and follow the path depicted by arrows 138. Thus, a single strand of cables enters the suspension system from a single location. The cable chains 134, 136 serve to retract the cables so that when the monitors 102 are moved from side to side, forwards, or backwards, the cables do not bunch up in the troughs 110, 115. Rather, the cable chains 134, 136 fold over onto themselves, which also allows them to be easily re-extended. To illustrate using FIG. 17, when a user slides the monitor display to the right (from the perspective of one facing the front of the monitors), the cable chain 136 will begin fold over onto itself. Then, when the user moves the monitor display to the left, the doubled-up cable chain 136 will unfold back into a single layer. Similarly, when a user slides the monitor display backward, the cable chain 134 will fold over onto itself. When the user slides the monitor forwards, the cable chain 134 will unfold. It is also important to note that even at the points where the cables are threaded through the cable chains 134, 136, they can be accessed due to the removable top or side surface of the chain (which can be easily pulled back to expose the cables within).

In so directing the cables, the following advantages can be realized: 1) the cables are not simply hanging out in the open creating potentially unsanitary conditions, and also potential risk for electric shock; 2) the cables, while not simply exposed, are nevertheless accessible for maintenance, repair, etc.; and 3) the cables are not prone to tangles by repeated back and forth or side to side movement.

Figure 5:
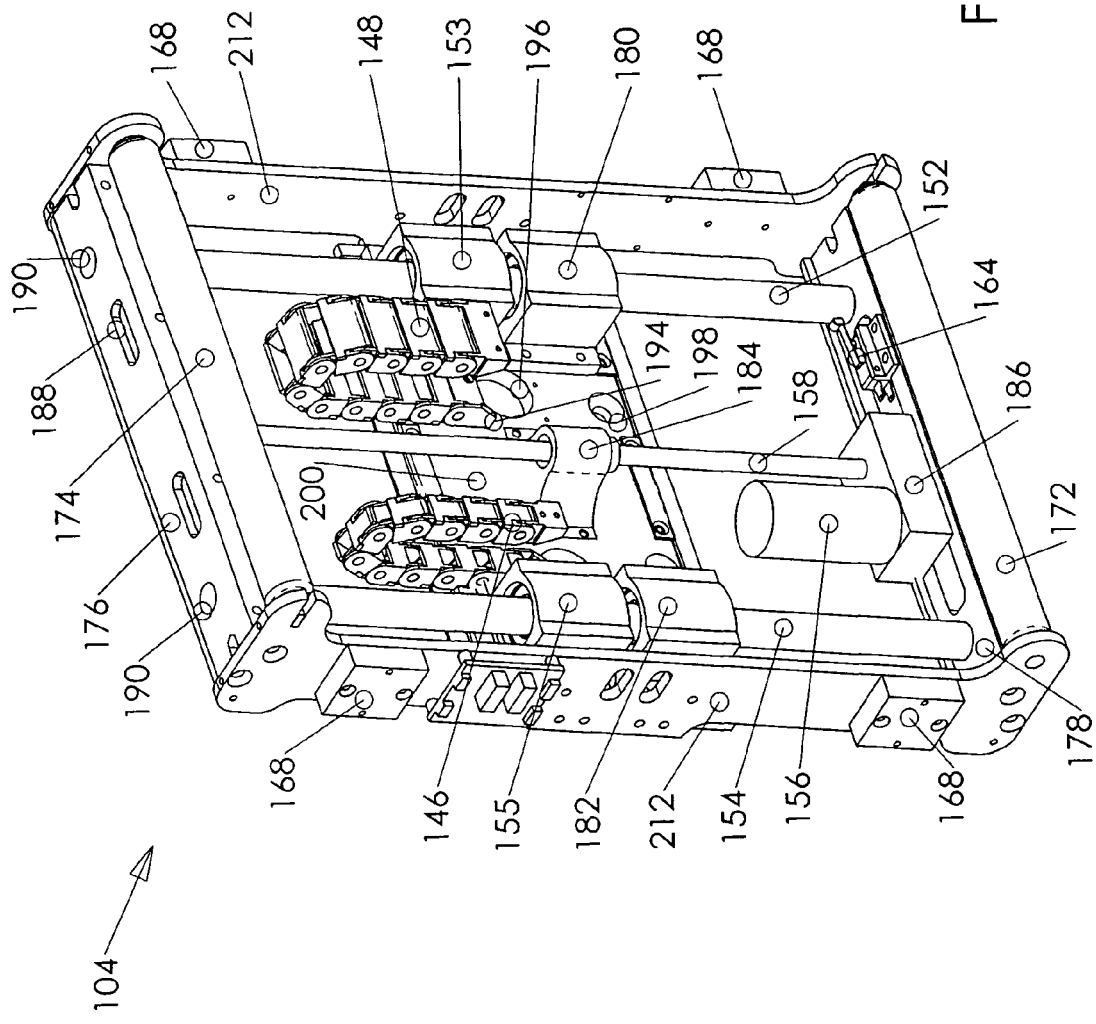
FIG. 5 shows a front perspective view of a component housing according to one embodiment of the present invention.

Referring now to FIGS. 5-11, the component housing 104 in this embodiment, includes an aluminum enclosure having a top plate 176, a bottom plate 178, and side plates 212. Inside the housing 104, as best seen in FIG. 5, is a cable chain 146 containing coaxial video feeds. In this embodiment, cable chain 148 contains the monitor power supply cables.

Figure 10:
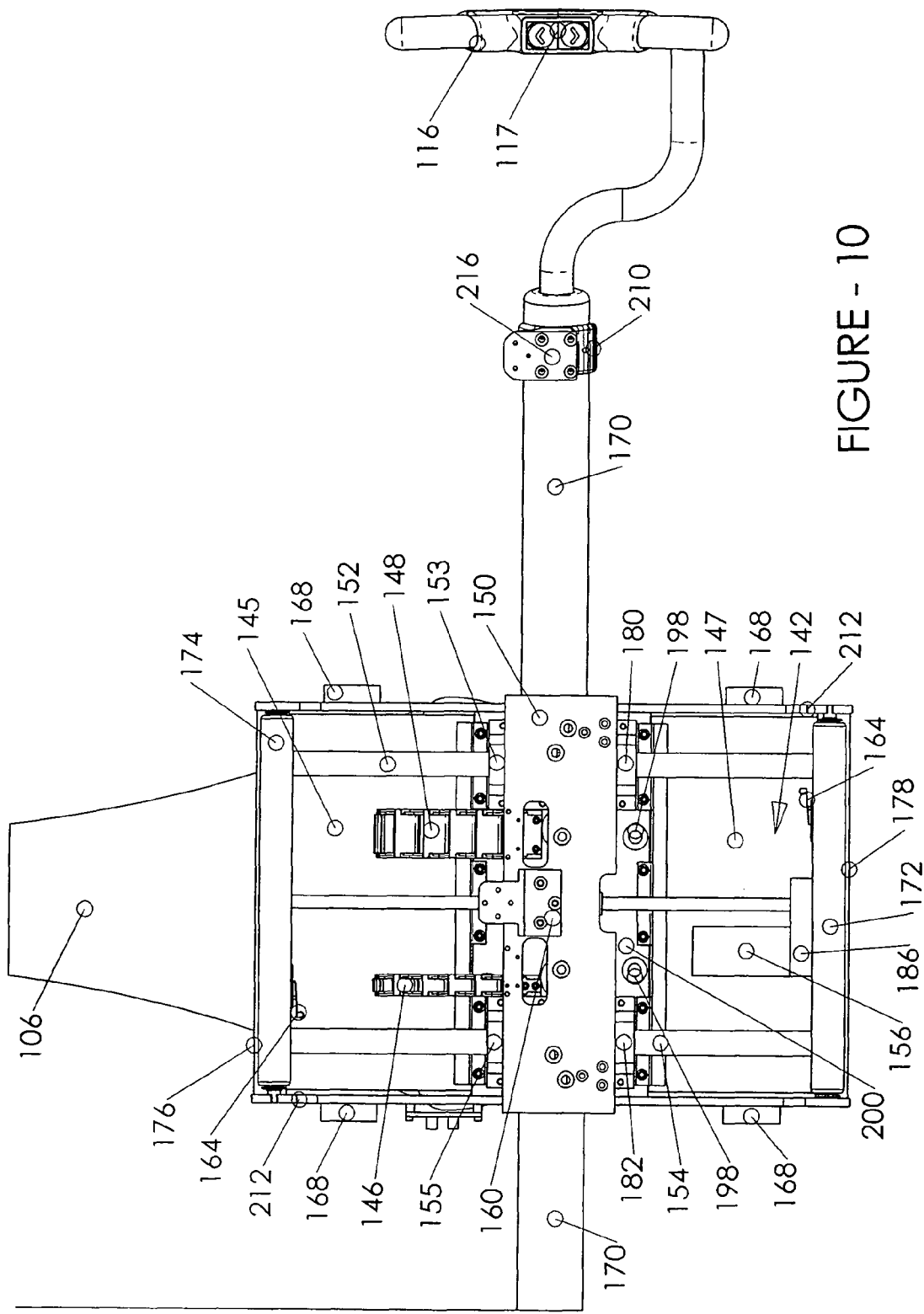
FIG. 10 shows the inside components of the component housing according to one embodiment of the present invention.

The cable chain 148 is coupled at one end to sliding plate 200 at point 194 (FIG. 5). Cable chain 146 is similarly coupled to the sliding plate 200 at one end. The other ends of the cable chains 146, 148 are coupled to face plate 150 (FIG. 10). As will be discussed further below, the coupling of the cable chains 146, 148 to both the sliding plate 200 and the face plate 150, allows for the orderly up and down movement of monitors 102.

The up and down movement is powered by an actuator motor 156, which is coupled to actuator screw 158. When the motor 156 turns the screw 158, it then drives the screw engagement 184 either up or down depending on the direction the screw is turning. The screw engagement 184 is coupled to the sliding plate 200. Thus, since sliding plate 200 remains stationary (as it is fixed to the suspension arm 106), as the screw 158 is turned, it raises or lowers the component housing 104 (depending on the direction it is being turned). During the up and down movement of the sliding plate 200 (or, perhaps more accurately, the movement of the component housing 104 relative to the sliding plate 200), the cable chains 146, 148 fold over onto themselves or unfold (depending on the direction of the movement), in a manner similar to the movement discussed in connection with cable chains 134, 136.

Bearings 153, 155 and bearing guides 152, 154 help ensure that the housing 104 is raised or lowered in a substantially vertical direction. Secondary bearings 180, 182 can also be included. This type of vertical movement using a screw-jack system is a significantly superior method over using telescopic arms, lift columns, or other similar elevating mechanisms. However, in certain embodiments, telescopic arms, lift columns, or other similar mechanisms for vertical movement of the display may be advantageous, and such embodiments are considered within the scope of the present invention.

In certain embodiments, the component housing 104 includes a decorative covering 105 (FIGS. 1, 3, 4, 16 and 17).

Figure 6:
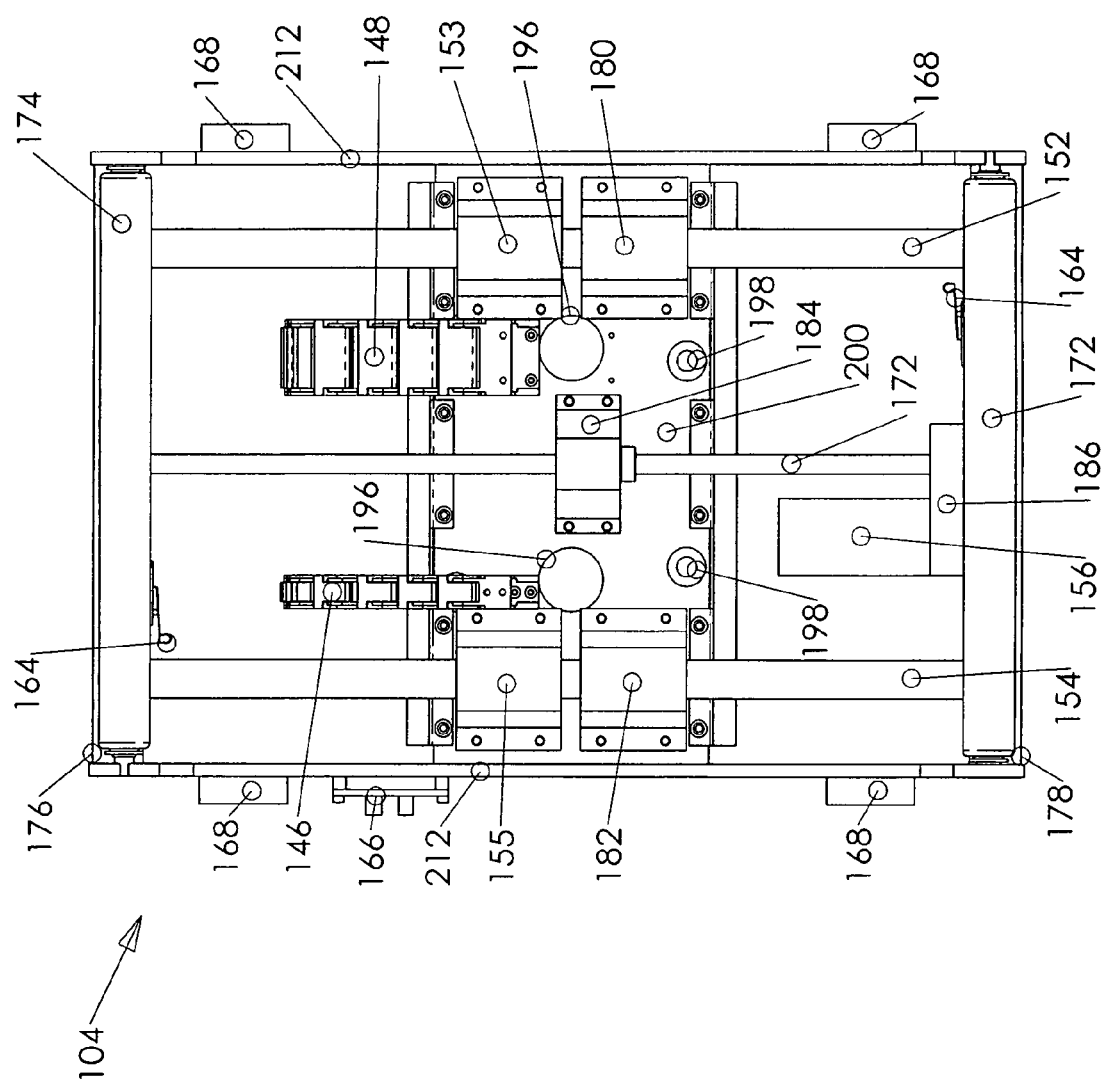
FIG. 6 shows a front view of a component housing according to one embodiment of the present invention.
Figure 7:
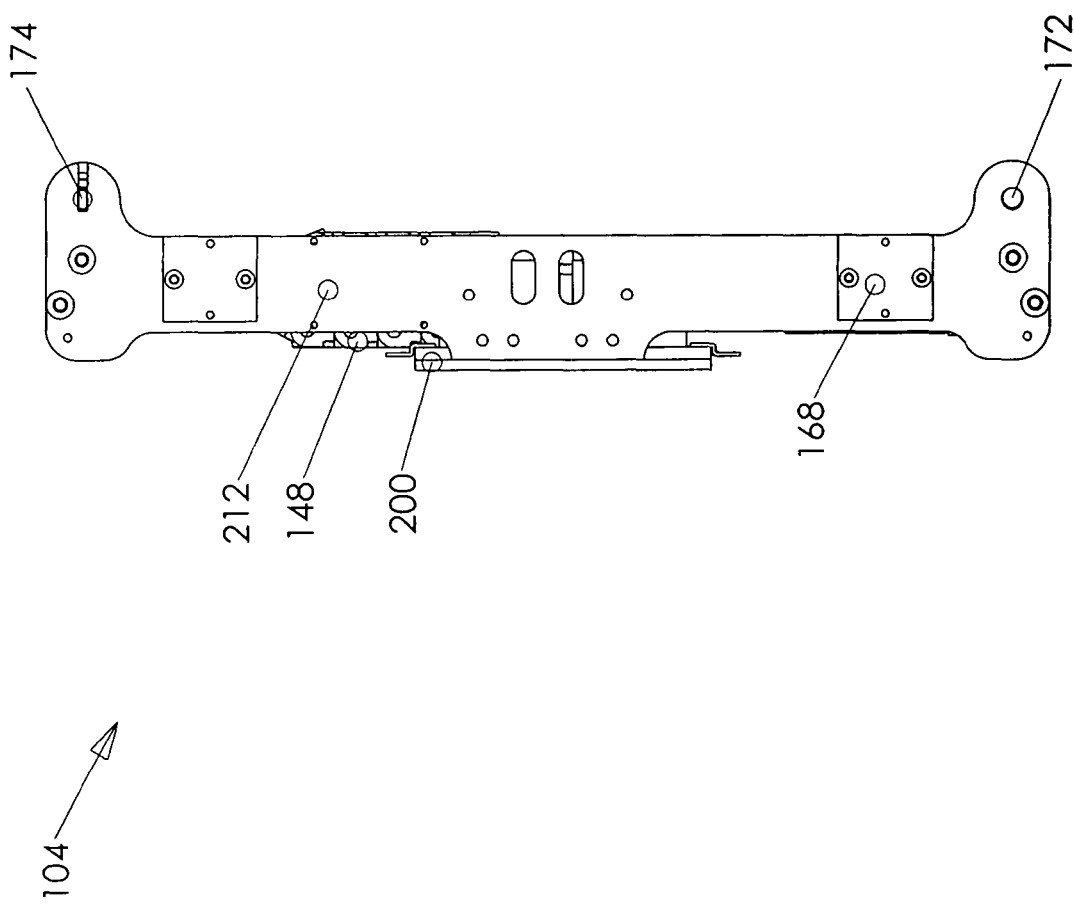
FIG. 7 shows a side view of the component housing depicted in FIG. 5.

As might be expected, the decorative covering 105 for the housing 104 is aesthetically advantageous (e.g. so that the mechanical parts of the housing 104 are not visible); it can also serve as a safety feature, in that it helps to keep users away from the mechanical parts of the housing 104. In the present embodiment, the covering 105 is attached to the housing 104 at spacers 168 (FIG. 6).

Figure 11:
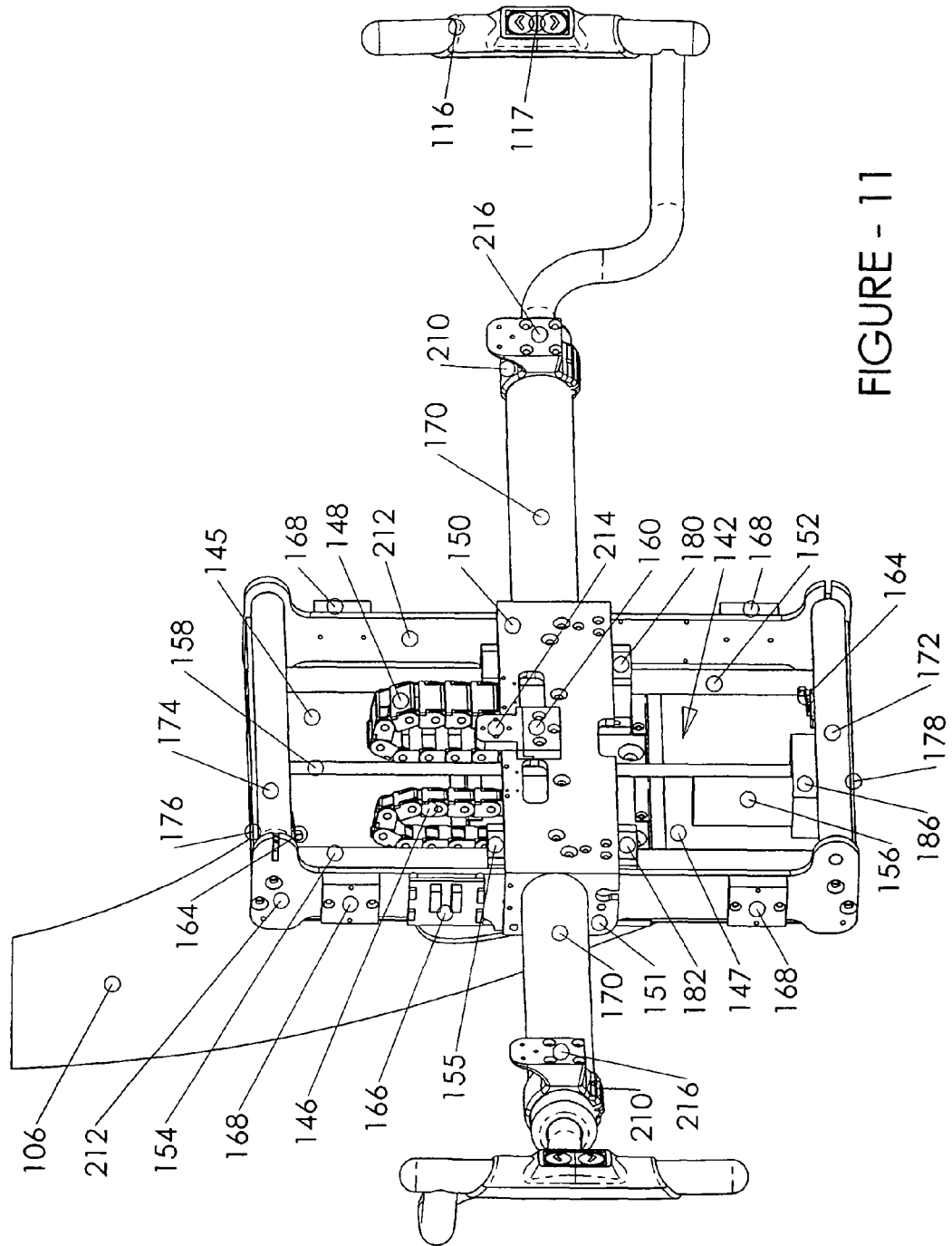
FIG. 11 shows a side-perspective view of the component housing depicted in FIG. 10.

In FIGS. 10 and 11, there is shown the face piece 150, on which is the mounting section 160. The mounting section 160 includes attachment 214 that, in the present embodiment, connects to the back of the monitor. In this embodiment, the face piece 150 includes side appendages 151 (FIG. 11) that wrap around the side plates 212 of the housing 104. This particular embodiment is made of aluminum. However, it could be made from numerous other materials, or combinations of materials, that would be apparent to one of ordinary skill in the art.

Mounting section 160 is where the first monitor 102 is attached. Supports 170 can also be included to enable the attachments of additional monitors 102. Specifically, the monitors 102 can be equipped with an attachment piece 216 that can be secured to supports 170. In this embodiment, the attachment piece 216 is secured to the support 170 by means of a sleeve 210 that wraps around the support 170. The supports 170 are made of steel or aluminum, but could also be made of numerous other materials, or combinations of materials, that would be apparent to one of ordinary skill in the art.

As is better seen in FIGS. 10 and 11, the face piece 150 and supports 170 can be manufactured as a single piece (a support piece assembly). In the present embodiment, the supports 170 are welded to the face piece 150 on the side appendages 151. Thus, when installing the combined face piece 150 and supports 170, one would simply rest the piece over the housing 104 and then fasten the appendages 151 to the side plates 212.

As is also seen in FIG. 11, handles 116 can include actuator buttons 117 that can be used to power the actuator motor 156 and direct the actuator screw 158 in an up or down direction.

Referring now to FIGS. 5-11 (to some of the smaller details of the present embodiments), the system 100 can include an actuator gear box 186 (FIGS. 5, 6, 10, 11). Holes 188 (FIGS. 5 and 9) allow for cable passage from the support arm 106 into the component housing 104 and specifically into cable chains 146 & 148 in this embodiment. Bolt holes 190 (FIGS. 8 and 9) are for attaching guide rails 154 & 152.

Counter Sunk bolt holes 198 (FIG. 10) are for coupling housing 104 to support arm 106 (in this embodiment, there are four total on plate 200). The present invention can also include wire passages 202 and 188—which are particularly useful in double tier configurations. The actuator mount base 204 (FIG. 8) is where the actuator gear box 186 is fastened to the bottom plate 178 of the housing.

Figure 8:
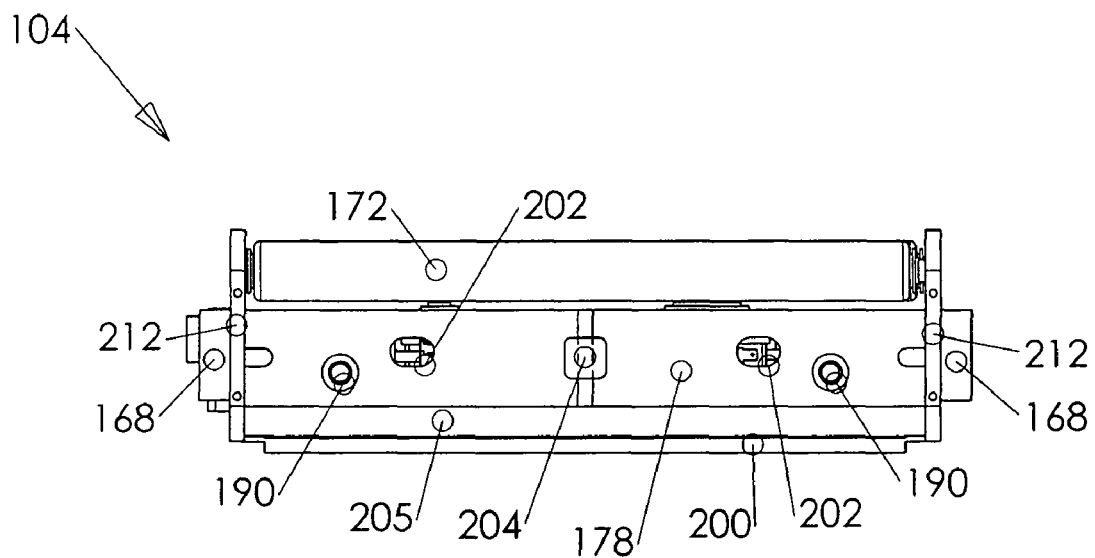
FIG. 8 shows a bottom view of the component housing depicted in FIG. 5.
Figure 9:
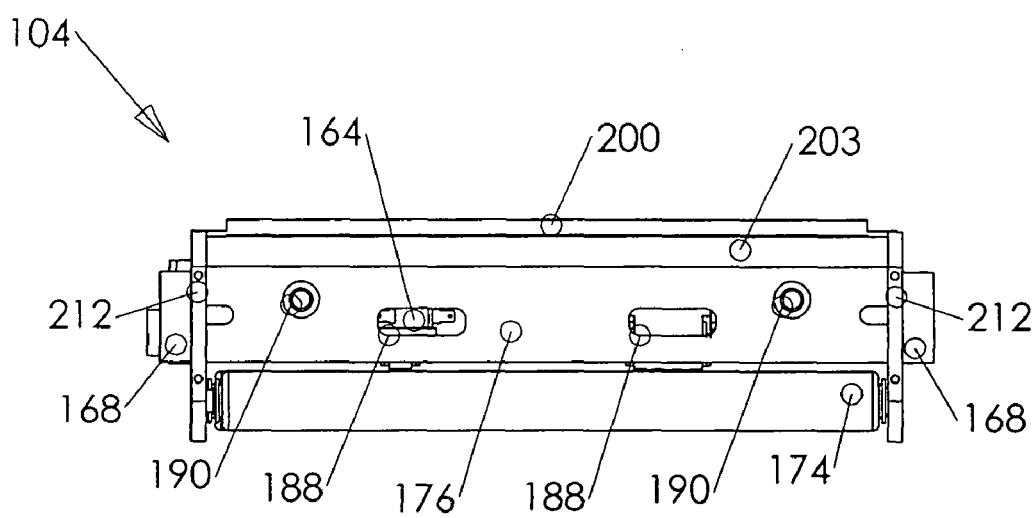
FIG. 9 shows a top view of the component housing depicted in FIG. 5.

Other possible features of the component housing 104 are a motor control board 166 (FIG. 11); limit switches 164 (FIG. 6)—which shut off power to the actuator motor 156 to prevent damage to the housing 104 from elevating or lowering it too far; relay switches 166 as part of the motor control board in the present embodiment (FIG. 11)—which facilitate the effective function of the limit switches 164 and allow for 5 volt buttons/switches 117 to operate 24 volt current relay; and rounded surfaces 203, 205 provide a smooth surface over which the vinyl cover 142 can make 90 degree turns (FIGS. 8 and 9).

In one embodiment, the housing 104 includes a vinyl back cover 142 (FIG. 4) that helps prevent accidental injury from exposure to the moving parts, and also adds aesthetic value to the device. The cover 142 in the present embodiment is actually two pieces. The first (top) piece 145 is fastened at one end to the upper roller 174 and at the other end to the top edge of the sliding plate 200. The second (bottom) piece 147 is fastened at one end to the lower roller 172 and at the other end to the bottom edge of the sliding plate 200. Couplings 230 (top) and 232 (bottom) are used to connect rollers 174, 172 to the sliding plate 200. The rollers 174, 172 have a spring recoil mechanism such that as the sliding plate 200 moves upward, the top piece 145 of the vinyl is drawn up around the roller 174. Likewise, when the sliding plate 200 moves downward, the bottom piece 147 of the vinyl is drawn up around the roller 172.

Figure 12:
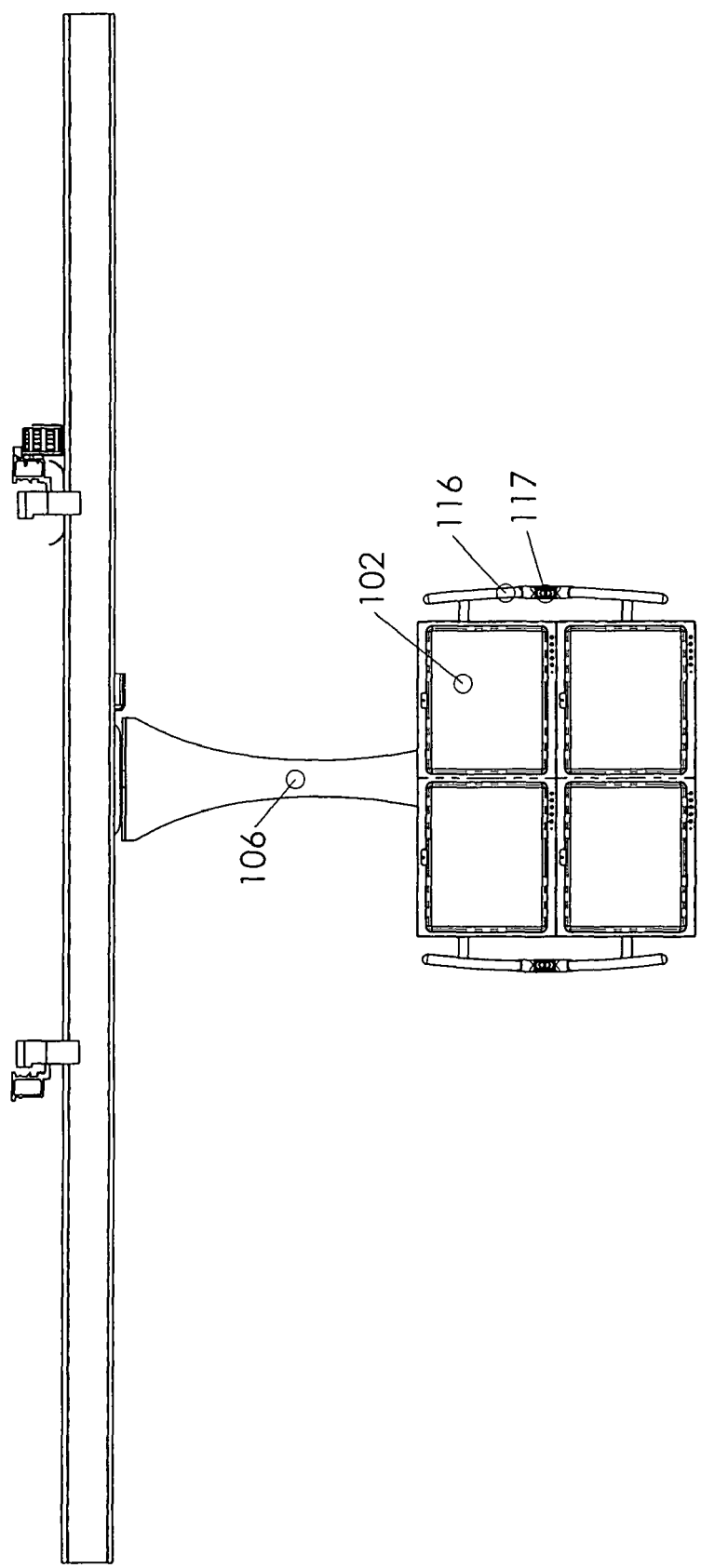
FIG. 12 shows a four-monitor suspension system according to yet another embodiment of the present invention.
Figure 13:
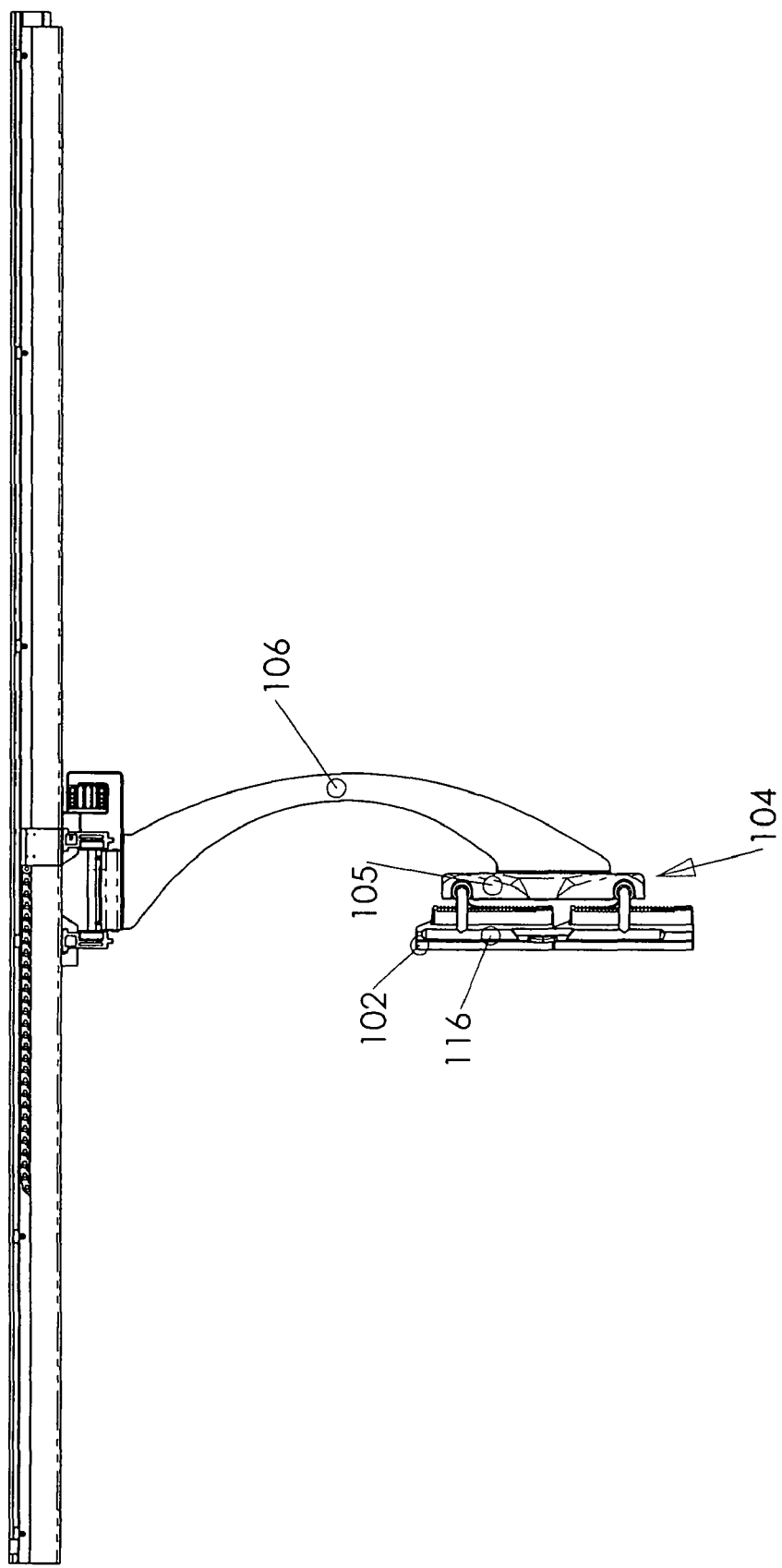
FIG. 13 shows a side view of the system depicted in FIG. 12.
Figure 14:
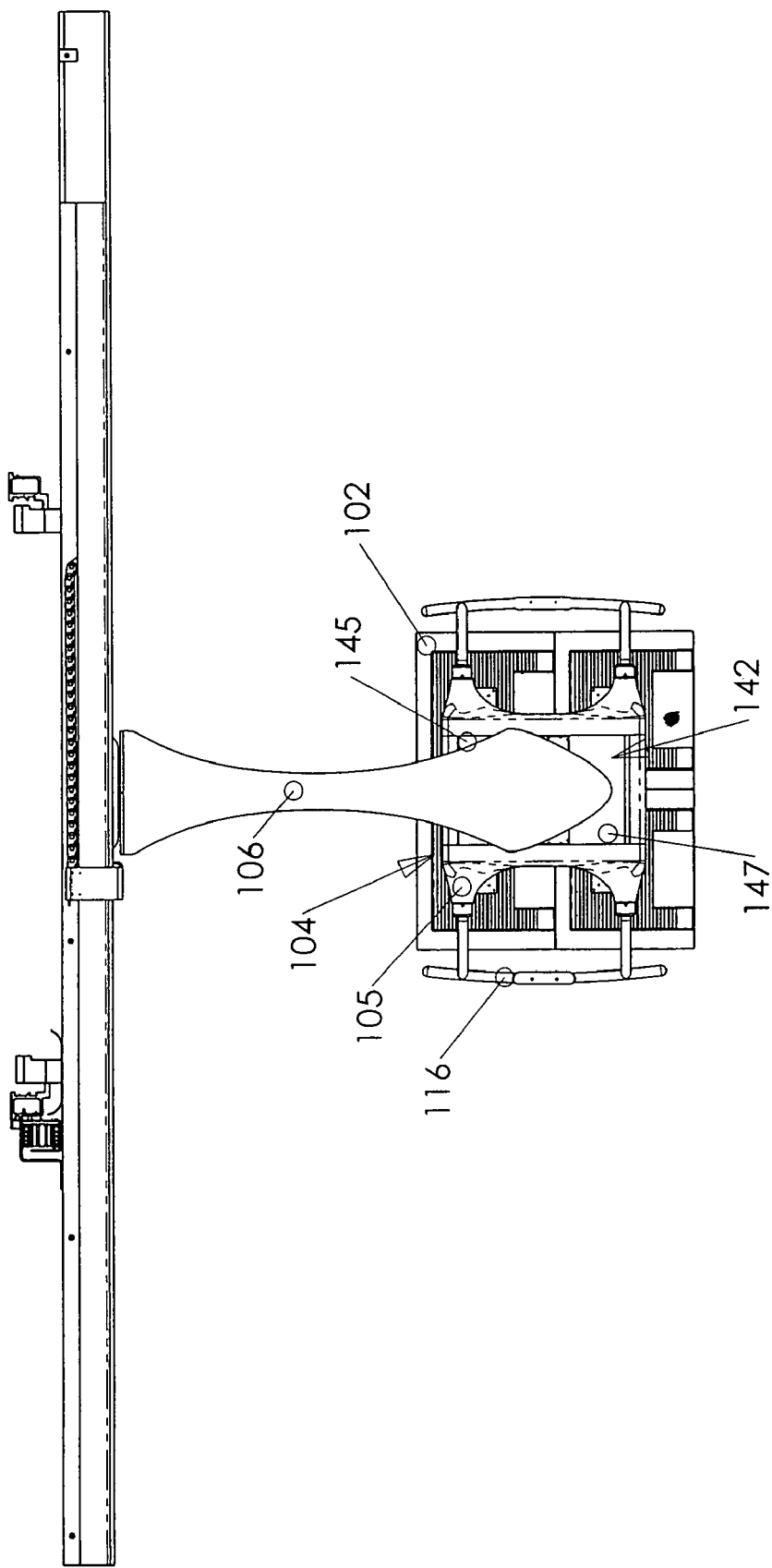
FIG. 14 shows a backside view of the system depicted in FIG. 12
Figure 15:
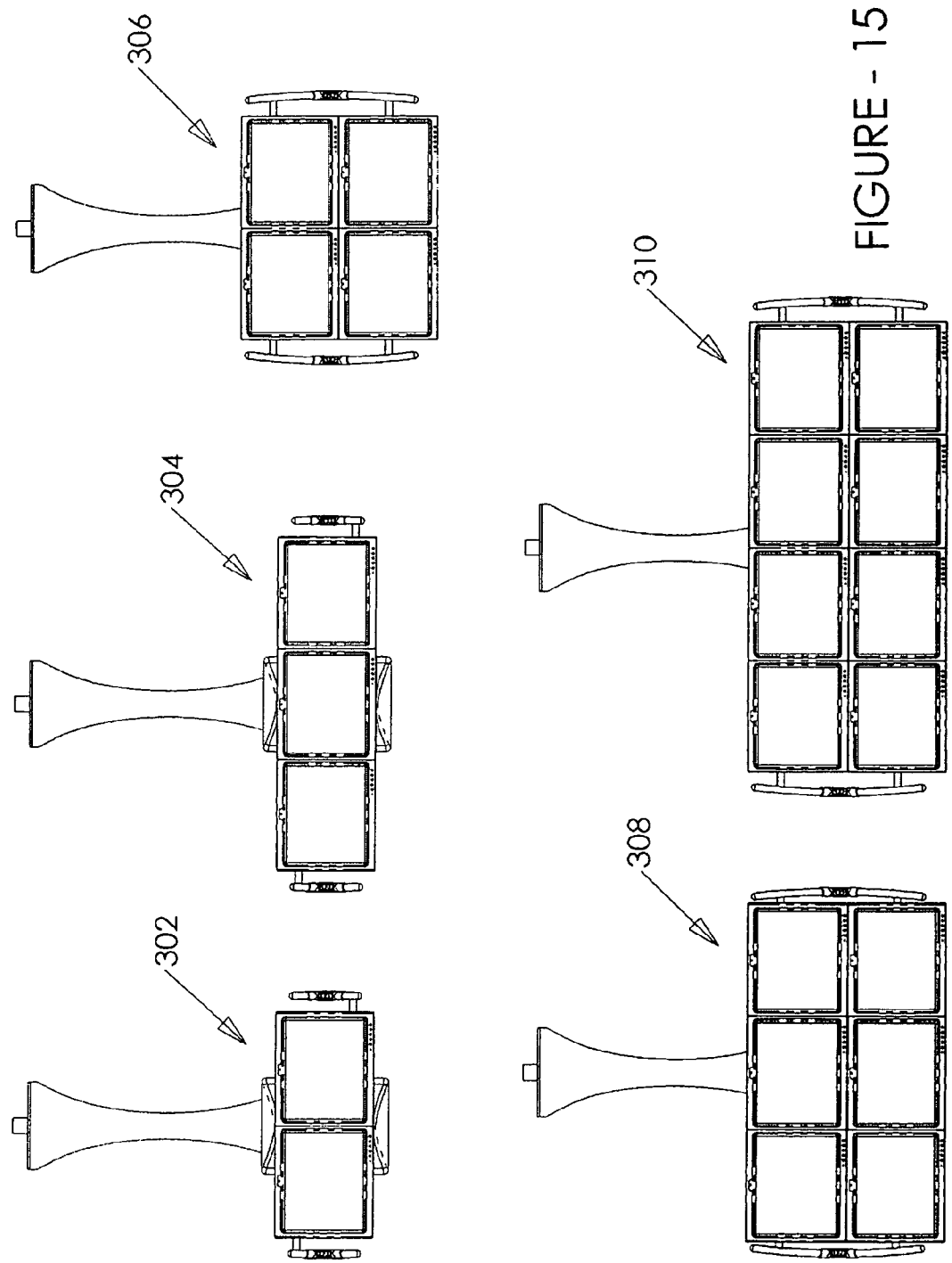
FIG. 15 shows various other potential embodiments of the present system.
Figure 16:
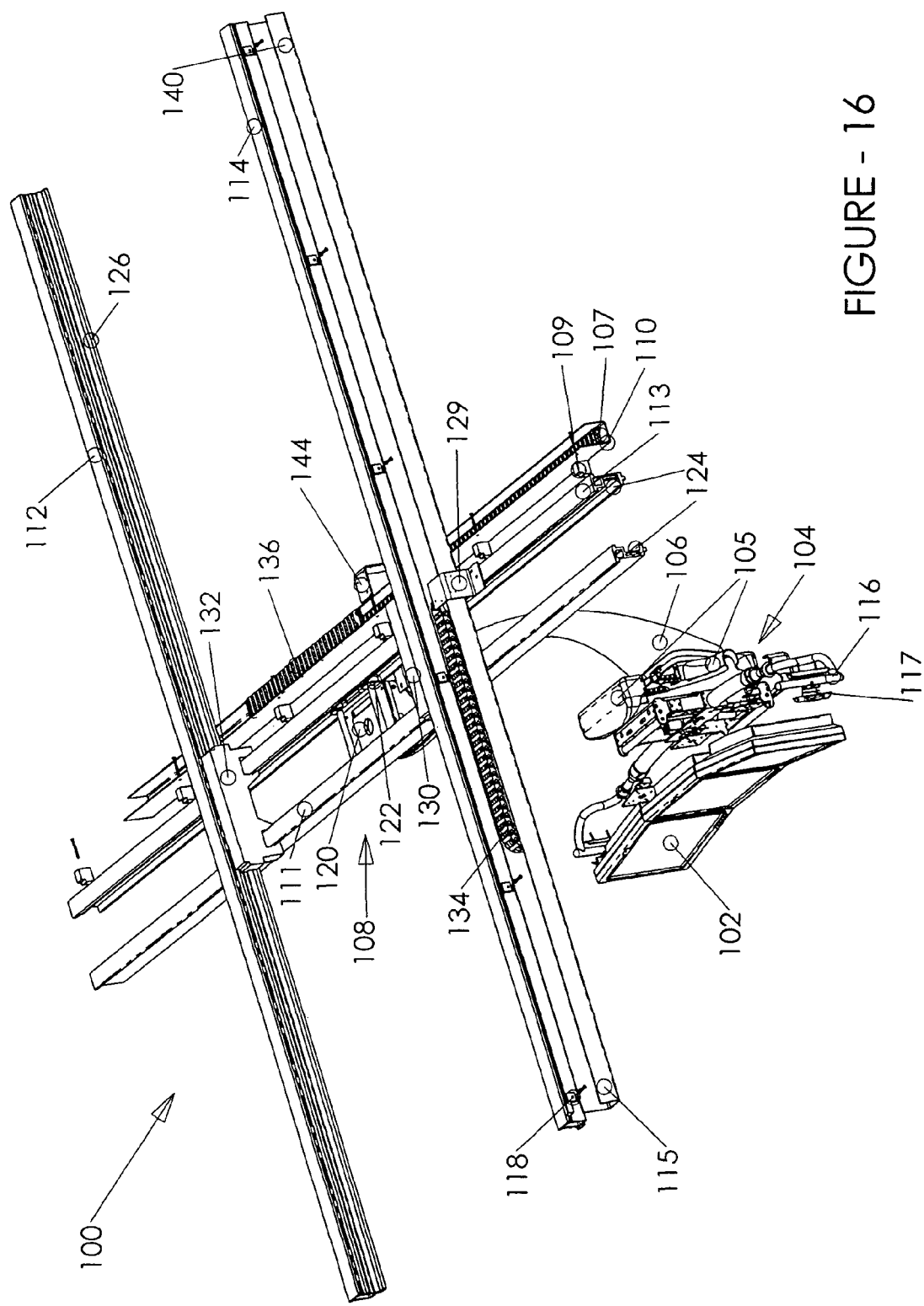
FIG. 16 shows a partially exploded view of a monitor suspension system according to one embodiment of the present invention.

Referring now to FIGS. 12-14, various views of a four-monitor suspension system are shown according to yet another embodiment of the present invention. In FIG. 15, is seen various other potential embodiments of the present system. Specifically, FIG. 15 shows a two monitor embodiment 302; a three monitor embodiment 304; a four monitor embodiment 306; a six monitor embodiment 308; and an eight monitor embodiment 310.

The suspension arm 106 in one embodiment is made of carbon fiber. The use of carbon fiber allows for a very strong yet lightweight suspension arm. The present medical monitor is also much more visually pleasing over anything in the prior art. Another advantage to the present system is that the center of gravity is placed directly under the suspension arm 106. As has been previously noted, the present system also allows for the elimination of draped cables through the cable chain system that retracts the cables as the monitors are moved in either the lateral or forward/backward direction. The present system also allows for easy cable inspection, replacement or repair.

The present system is especially well suited for use with LCD monitors. However, other monitor types could be used in connection with the present system, including, but not limited to plasma, OLED and other types of monitors. In certain embodiments, the system utilizes VGA over Cat-5 (or Cat-6) type cable system for SVGA/VGA displays.

Figure 18:
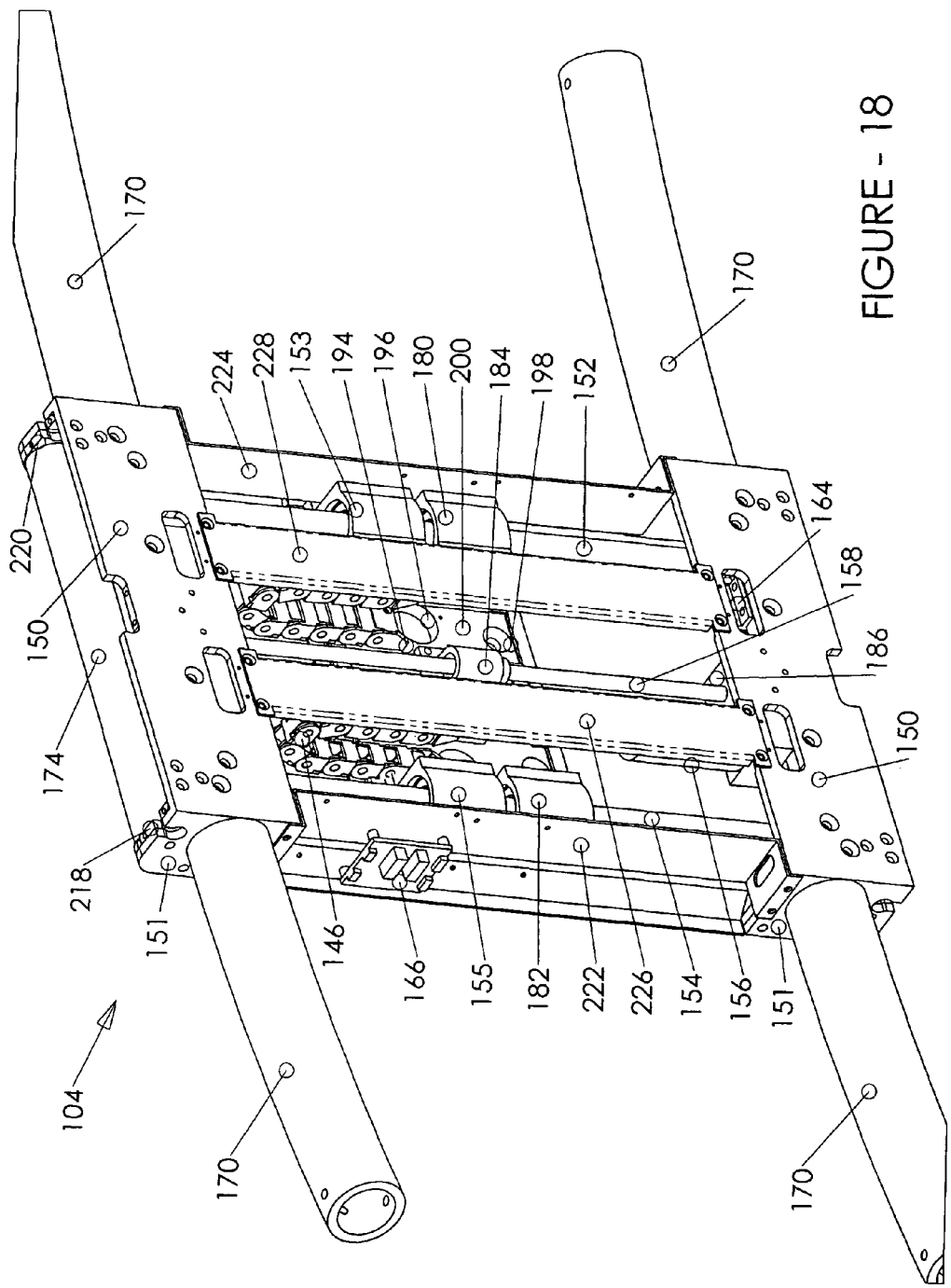
FIG. 18 shows yet another embodiment of a component housing according to one embodiment of the present invention.
Figure 19:
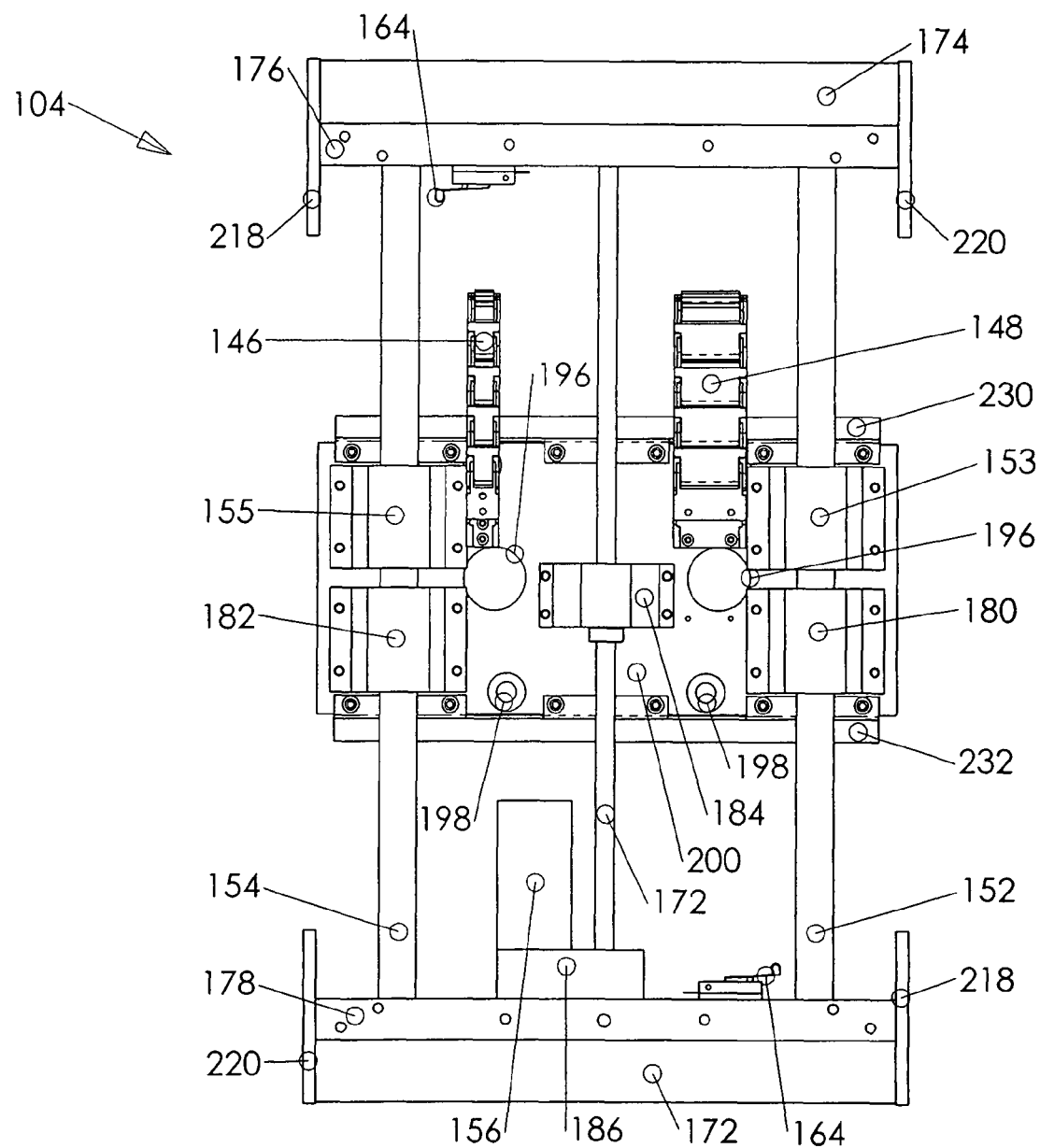
FIG. 19 shows a front view of the component housing depicted in FIG. 18.
Figure 20:
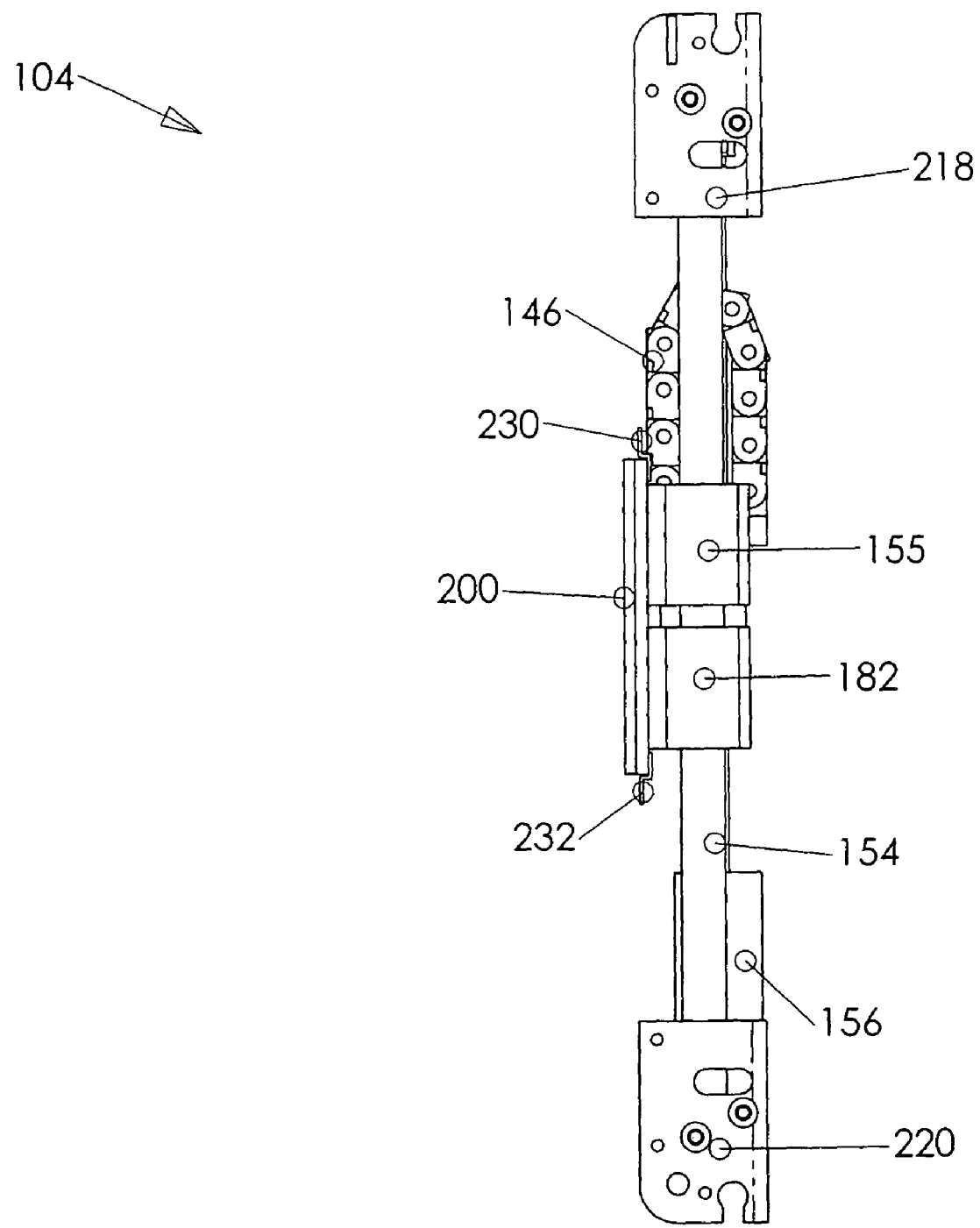
FIG. 20 shows a side view of the component housing depicted in FIG. 18.

Referring to FIGS. 18-20, there is shown a component housing 104 for a multi-tiered monitor suspension system. As can be appreciated, a multi-tiered system would, of necessity, have some unique adaptations of the present system. For example, in this embodiment, there are two support piece assemblies (as discussed in connection with FIGS. 10 and 11 above). These support piece assemblies likewise include the face piece 150 and supports 170 welded to the face piece 150 on the side appendages 151. In this embodiment, rollers 174 and 172 are mounted on the assemblies. These support piece assemblies are coupled to side plates 218, 220.

Couplings 222, 224 allow for additional audio/video components to be mounted to the system. They also allow for the passage of wires. These couplings 222, 224 are made of steel, but as would be apparent to one skilled in the art, could be made of other materials or combinations of materials. This embodiment also includes strips 228, 226 that help keep cable chains restrained. In this embodiment, the strips are made of sheet metal, but, as would be apparent to one skilled in the art, could be made of numerous other materials or combinations of materials. It is also noted that these strips can act as a track. And in certain embodiments, the cable chains 146, 148 could be directly mounted to these strips 228, 226 (instead of plate 150).

VARIATIONS OF THE PRESENT INVENTION

It is understood that the above-described embodiments are only illustrative of the application of the basic principles of the present invention. Numerous modifications and alternative arrangements may be devised by those skilled in the art without departing from the spirit and scope of the present invention.

For example, in one embodiment there may be only a single lateral track. In yet another embodiment, there could be a single backward/forward track. In yet other embodiments, movement may only be desired in a single direction (e.g. lateral only, or backward and forward only).

In one embodiment, the suspension arm could be made of fiberglass, aluminum, steel, or numerous other materials that would be apparent to one of ordinary skill in the art. As previously noted, the component housing could be a separate piece as is shown in the figures; or it could be integrated directly into the suspension arm.

What is claimed is:

1. A monitor suspension system comprising:
 a) a suspension arm having a first and second end;
 b) a component housing coupled to the first end of the suspension arm, having:
  i) a top plate;
  ii) a bottom plate;
  iii) one or more side plates;
  iv) a face piece, including one or more side appendages that are capable of wrapping around the side plates of the component housing and having one or more supports coupled thereto, whereupon one or more additional monitors may be attached;
  v) a sliding plate;
  vi) one or more cable chains coupled at a first end to the sliding plate and at a second end to the face piece; and
  vii) an actuator motor coupled to the sliding plate; wherein the actuator motor drives up and down movement of the component housing;
 c) a lateral carriage assembly coupled to the second end of suspension arm, and wherein the lateral carriage assembly includes:
  i) a first lateral track;
  ii) a lateral trough coupled to the first lateral track;
  iii) a second lateral track;
  iv) a lateral movement piece which is slidably coupled between the first lateral track and the second lateral track;
 d) a first backward/forward track;
 e) a second backward/forward track;
 f) a backward/forward trough coupled to the first backward/forward track;
 g) a first front/back sliding assembly coupled to the lateral carriage assembly and capable of slidably engaging the first front/back track;
 h) a second front/back sliding assembly coupled to the lateral carriage assembly and capable of slidably engaging the second front/back track;
 i) a first cable chain coupled at a first end to the backward/forward trough and coupled at a second end to the lateral carriage assembly; and
 j) a second cable chain coupled at a first end to the lateral trough and coupled at a second end to the lateral movement piece.

2. The system of claim 1, wherein the face piece further comprises a monitor mounting section.

3. The system of claim 1, wherein the face piece and one or more supports are a single piece.

4. The system of claim 1, further including one or more handles coupled to the supports.

5. The system of claim 4, further comprising one or more actuator buttons on the handles.

6. The system of claim 1, wherein the first backward/forward track is coupled to a building support structure.

7. The system of claim 1, wherein the lateral movement piece further includes one or more wheels capable of engaging one or more grooves in the first and second lateral tracks.

8. A monitor suspension system comprising:
   a) a component housing having:
      i) a top plate;
      ii) a bottom plate;
      iii) one or more side plates;
      iv) a face, piece, including one or more side appendages that are capable of wrapping around the side plates of the component housing and having one or more supports coupled thereto, whereupon one or more additional monitors may be attached;
      v) a sliding plate;
      vi) one or more cable chains coupled at a first end to the sliding plate and at a second end to the face piece; and
      vii) an actuator motor coupled to the sliding plate; wherein the actuator motor is coupled to the sliding plate by means of a screw engagement piece, which is in communication with a screw that is rotatably coupled to the top and/or bottom plate, and which is turned by motor, thereby directing up and down movement of the component housing; and
   b) a suspension arm coupled at a first end to the sliding plate.

9. The system of claim 8, wherein a second end of the suspension arm is slidably coupled to a track.

10. The system of claim 9 further comprising a length of cable chain in communication with the track; wherein the cable chain is capable of foldably retracting as the suspension arm is slid along the track; and through which one or more monitor cables are conducted.

11. The system of claim 8, wherein the face piece further comprises a monitor mounting section.

12. The system of claim 8, wherein the face piece and one or more supports are a single piece.

13. A monitor suspension device comprising:
   a) a suspension arm having a first and second end;
   b) a component housing coupled to the first end of the suspension arm, having one or more side plates;
   c) a face piece having one or more side appendages that are capable of wrapping around the side plates; and
   d) one or more supports coupled to the side appendages having one or more handles coupled thereto, and whereupon one or more additional monitors may be attached.

14. The device of claim 13, wherein the face piece and one or more supports are a single piece.

15. The device of claim 13, wherein the face piece further comprises a monitor mounting section.

16. The device of claim 13, wherein the second end of the suspension arm is slidably coupled to a track.

17. The device of claim 16 further comprising a length of cable chain in communication with the track; wherein the cable chain is capable of foldably retracting as the suspension arm is slid along the track; and through which one or more monitor cables are conducted.

\* \* \* \* \*